(12) United States Patent  
Ziarati

(10) Patent No.: US 9,571,820 B2  
(45) Date of Patent: Feb. 14, 2017

(54) MRI-COMPATIBLE 3D TELEVISION AND DISPLAY SYSTEM

(71) Applicant: Resonance Technology, Inc., Northridge, CA (US)

(72) Inventor: Mokhtar Ziarati, Porter Ranch, CA (US)

(73) Assignee: Resonance Technology, Inc., Northridge, CA (US)

( * ) Notice: Subject to any disclaimer, the term of this patent is extended or adjusted under 35 U.S.C. 154(b) by 1090 days.

(21) Appl. No.: 13/725,339

(22) Filed: Dec. 21, 2012

(65) Prior Publication Data

US 2013/0182085 A1 Jul. 18, 2013

Related U.S. Application Data

(60) Provisional application No. 61/582,323, filed on Dec. 31, 2011, provisional application No. 61/729,457, filed on Nov. 23, 2012.

(51) Int. Cl.
| | |
|---|---|
| H04N 13/00 | (2006.01) |
| H04N 13/04 | (2006.01) |
| A61B 5/055 | (2006.01) |
| H05K 9/00 | (2006.01) |
| A61B 5/00 | (2006.01) |

(52) U.S. Cl.  
CPC ............ *H04N 13/04* (2013.01); *A61B 5/0046* (2013.01); *A61B 5/055* (2013.01); *H05K 9/0054* (2013.01); *H04N 13/0434* (2013.01); *H04N 2213/001* (2013.01)

(58) Field of Classification Search  
USPC ................................................ 348/42–44, 51  
See application file for complete search history.

(56) References Cited

U.S. PATENT DOCUMENTS

| | | | |
|---|---|---|---|
| 5,412,419 A | 5/1995 | Ziarati | |
| 5,432,544 A | 7/1995 | Ziarati | |
| 5,627,902 A | 5/1997 | Ziarati | |
| 5,877,732 A | 3/1999 | Ziarati | |

*Primary Examiner* — Nigar Chowdhury  
(74) *Attorney, Agent, or Firm* — Larry K. Roberts

(57) ABSTRACT

A display system compatible with a magnetic resonance imaging (MRI) apparatus disposed in a magnet room for producing video images to a patient in an MRI magnet tunnel, the images having a three-dimensional (3D) effect. An MRI-compatible 3D display includes a display panel configured to generate optical images having 3D content, and RF and electromagnetic interference filtering. A Faraday cage encloses the display panel, and includes an optically transparent window panel having an electrically conductive mesh and a layer of transparent optically isotropic material.

14 Claims, 5 Drawing Sheets

MRI-COMPATIBLE 3D TELEVISION AND DISPLAY SYSTEM

CROSS-REFERENCE TO RELATED APPLICATIONS

This application claims priority from U.S. Provisional Application No. 61/582,323, filed Dec. 31, 2011, and from U.S. Provisional Application 61/729,457, filed Nov. 23, 2012, the entire contents of which applications are hereby incorporated by reference.

BACKGROUND

The use of displays in a Magnetic Resonance Imaging (MRI) equipment environment was first developed in the late 80's and early 90's, as described in U.S. Pat. No. 5,412,419, 5,432,544, 5,627,902, and 5,877,732.

The earliest form of three dimensional (3D) technology first appeared in the movie industry at the end of the 19th century. The principal concept of this technology is to recreate the way humans see depth in real life; through a phenomenon called "binocular fusion". 3D TVs digitally recreate the perception of binocular fusion to give viewers an immersive viewing experience with pictures that pop off the screen. With the recent release of new 3D TVs to the market, together with readily available 3D movies and other content, it would be advantageous to bring this new technology to patients in the MRI environment.

BRIEF DESCRIPTION OF THE DRAWINGS

Features and advantages of the disclosure will readily be appreciated by persons skilled in the art from the following detailed description when read in conjunction with the drawing wherein:

FIG. 3B illustrates features within circle 3B of FIG. 3.

DETAILED DESCRIPTION

Figure 1:
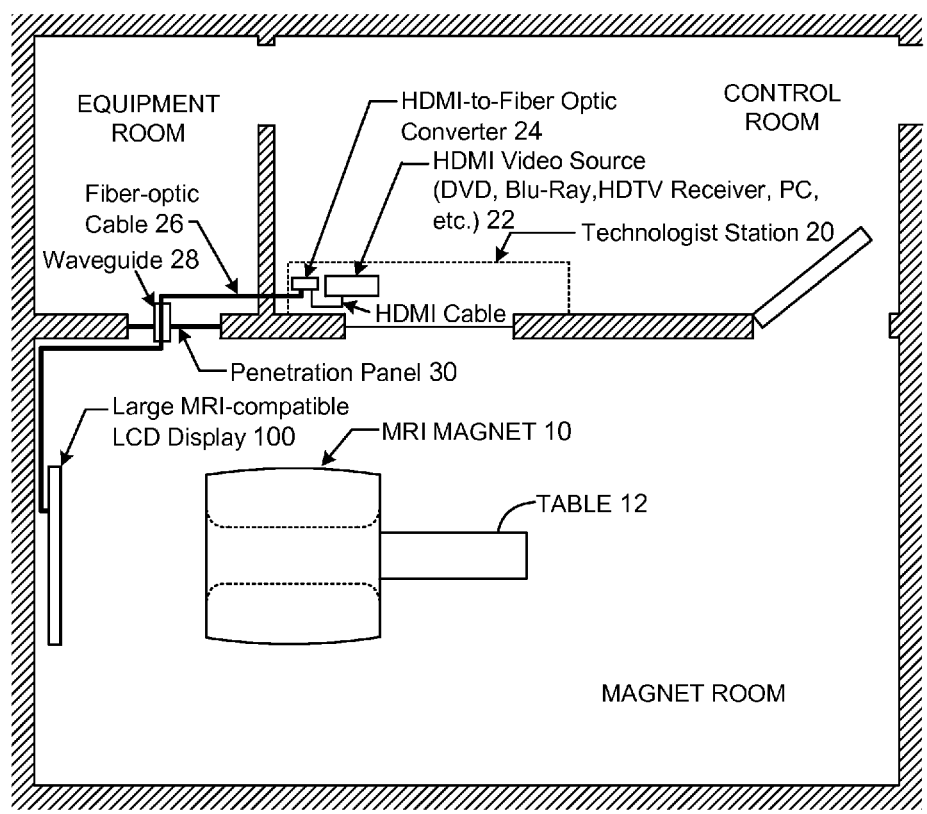
FIG. 1 is a schematic illustration of a 3D LCD monitor setup in an MRI suite.

In the following detailed description and in the several figures of the drawing, like elements are identified with like reference numerals. The figures are not to scale, and relative feature sizes may be exaggerated for illustrative purposes.

A 3D TV and the human eye have a lot in common. Since our eyes are spaced slightly apart, the left and right eye sees images from a slightly different perspective. The human brain then combines the two images to create a 3D impression. A 3D TV works the same way. Two images—displayed from slightly different angles—are viewed through 3D glasses and then combined by the brain to construct a 3D image The first generation of 3D shutter glasses produced a 3D effect, in part, with technology embedded in the glasses. 3D shutter glasses function just like a camera shutter. A 3D television, in synchronization with the 3D glasses, alternately flashes a 2D image to each eye through a liquid crystal layer embedded within each lens of the glasses. The viewer's brain then combines the images flashed to each eye to create a 3D effect. However, the use of 3D shutter glasses in an MRI magnet room application is useless due to the electronics and battery existing in the active shutter glasses.

The next generation FPR (Film Patterned Retarder) 3D relies on technology embedded in the television. FPR 3D glasses use a circular polarized filter to present two images concurrently to each eye. FPR 3D TVs incorporate the FPR technology in which a polarized film is placed on the 3D television screen to effectively split the left and right images into interweaving odd and even lines onscreen, and along with the 3D glasses which use circular polarization filters of opposite sense, separates the left and right images before they are delivered to the brain. This technically halves the original resolution of 3D content to each eye. The images are then combined by the brain to create the 3D impression. The applicant has recognized that this technology is ideal for use in MRI applications.

An LCD TV can be shielded to block the emission of electromagnetic interference (EMI) inside of the MRI room, to provide an MRI-compatible display. For example, the front active part of the LCD TV may be shielded with a micro conductive mesh or laser aided conductive mesh which is 30 micrometers thick and will not appear when viewed with the naked eye. The entire LCD monitor will then be housed in a shielded Faraday cage, with inputs for power and the video/audio signals (e.g. carried by fiber optics or by Wi-Fi signals).

FIG. 1 illustrates a typical component layout within the MRI suite. In this exemplary layout, the MRI magnet is disposed in the magnet room, with a patient table for positioning the patient in the bore of the MRI magnet 10. An MRI-compatible 3D display such as a large MRI-compatible LCD display 100 is positioned on a wall in the magnet room at a position selected to allow the patient in the MRI bore to observe the display, with the aid of a mirror. In this exemplary embodiment, the MRI-compatible 3D display is a display 100 which employs FPR technology to provide a 3D effect when used with an appropriate set of goggles or glasses, with circular polarization filters of opposite sense through which the image generated by the 3D display is viewed.

The control room includes the Technologist Station 20 for controlling the MRI system. An FPR-compatible video source 22 capable of generating signals to produce the 3D image is placed in the control room, and its signal is converted (e.g. through an HDMI-to-Fiber Optic Converter 24) to an optical signal carried on an optical fiber 26. The video source may be, for example, a DVD player, HDTV receiver, a PC, etc. The optical fiber is passed from the control room into the equipment room and through a waveguide 28 positioned in a penetration panel 30 to the magnet room and to the large MRI-compatible LCD display 100. Alternatively, in another embodiment, the video source signals may be broadcast using a Wi-Fi broadband network, wherein a Wi-Fi repeater is used to transmit signals (e.g. from an antenna mounted to the magnet room wall).

Figure 2:
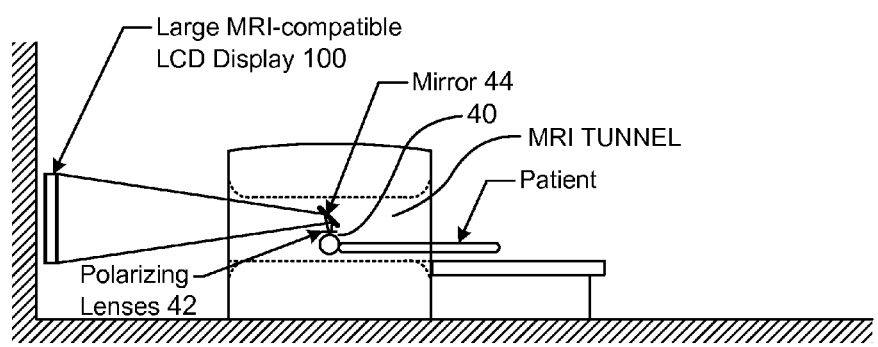
FIG. 2 is a diagrammatic cross-sectional view of an exemplary embodiment of a system for 3D display delivery in the MRI.

FIG. 2 illustrates the patient setup for the system in further detail. The patient wears the circular polarized passive glasses or goggles 40, with lenses 42 having circular polarization filters of opposite polarization sense for the left and right eye, typically applied by a filter film, and through the use of a reflective mirror 44, can view the 3D MRI-compatible display (e.g. a shielded 3D LCD TV) located on either end of the MRI bore (tunnel). The patient goggles 40 are configured to be MRI-compatible and fabricated without magnetic materials. Alternatively the circularly polarized filters can be built into the passive goggles or applied to the mirror 44 into which the patient looks to see the display image. The patient goggles are typically fabricated of a very thin layer of optically clear plastic on which the filters are formed, and, because of the thinness, do not affect substantially the 3D image quality.

In exemplary embodiments, the display 100 may be a large screen high definition 3D display or TV, utilizing LCD, LED or OLED technology (i.e. a 3D HD TV) and images generated by the display are relayed to the subject via a reflective mirror applied to a rear surface of a substrate formed of optically isotropic material. Alternatively, this could be a front surface mirror.

In an exemplary embodiment for use in an MRI magnet room, the 3D TV is housed in a non-magnetic Faraday cage to shield EMI. A clear conductive window overlay is specially made for the MRI 3D application utilizing FR technology, where it is optically clear or transparent and does not affect screen polarization.

The process of making the conductive window for the display in one exemplary embodiment uses a very fine conductive mesh laminated between two layers of optically isotropic glass or plastic material in a way that the edge of the mesh at the window edges is exposed. A conductive adhesive such as silver epoxy is applied to the mesh and window edges. By applying the silver epoxy, all the window edges become shorted to the mesh, increasing a surface area of conductive material in electrical contact with the mesh. With the conductive window assembled in the housing, the edge of the conductive window stays in tight contact with the housing of the display. For the 3D system to operate properly, the base material of any adhesive or other structures used to build the window may not cause interference with the polarization of the TV. Optically isotropic materials are used for the rf (radio frequency) conductive window on the display and the reflective mirror (i.e. materials having the same optical properties in all directions). The mesh may be sandwiched between the two layers of the window because the mesh is very fine and to protect it from damage.

Another alternative for constructing the fine mesh is to start with a sheet of conductive copper applied to a glass layer, and then etch away most of the copper, leaving only a very fine line in the shape of very fine mesh. The etching may be done by a laser or other etching techniques.

Figure 3A:
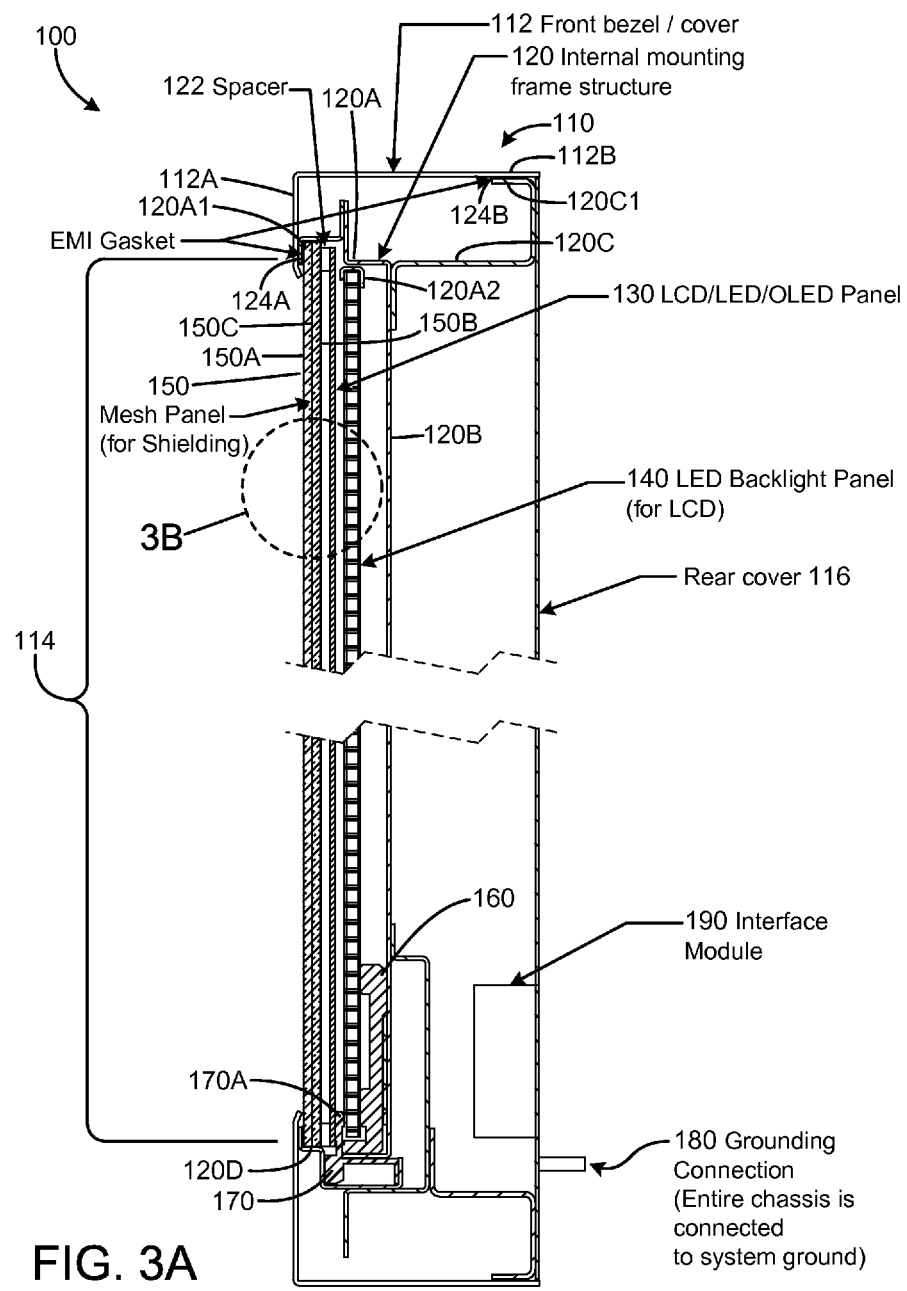
FIGS. 3A and 3B are cross-sectional diagrammatic illustrations of an exemplary embodiment of a 3D display.
Figure 3B:
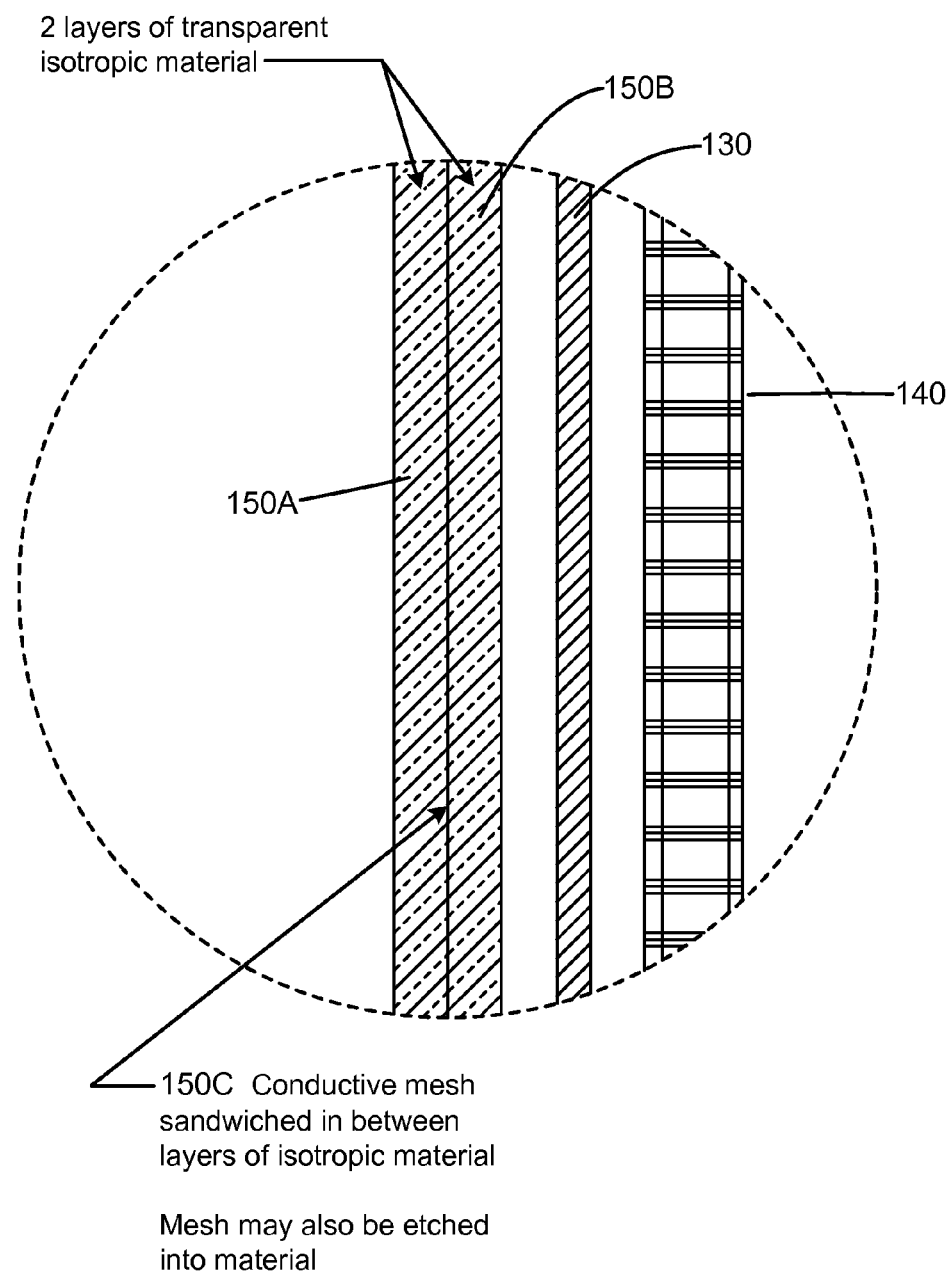

FIG. 3A is a diagrammatic cross-sectional view illustrating features of an exemplary embodiment of a 3D flat panel display 100 suitable for use in the magnet room environment of FIGS. 1 and 2. FIG. 3B illustrates features within circle 3B of FIG. 3A. The display is constructed to provide a Faraday cage 110 defined by non-magnetic, electrically conductive materials. The Faraday cage 110 includes a front bezel or cover structure 112 which circumscribes the display panel area 114, and rear cover 116. The cover structure 112 may be fabricated of a non-magnetic electrically conductive material such as, by way of example only, brass or aluminum. The rear cover 116 attaches to the back of the cover structure 112. The Faraday Cage 110 includes an internal mounting frame structure 120 which is positioned between the inside of the front bezel portion 112A of the cover structure 112 and the rear cover 116. The rear cover and the internal mounting frame structure are also fabricated of non-magnetic electrically conductive material, such as brass or aluminum.

The internal mounting frame structure 120 and the cover structure 112 are configured to support the planar display system components, including the LCD/LED/OLED display panel 130, an LED backlight panel 140 (for an LCD implementation), and a mesh panel assembly 150 to cover the display panel or window area 114. The display panel may be a flat panel display such as an LCD (liquid crystal display) panel, an LED (light emitting diode) panel, an OLED (organic light emitting diode) panel, or even a plasma panel, for example. In the case of an LCD display panel, the backlight panel 140 is provided behind the display panel 130. The backlight panel 140 may be omitted for the implementation in which the display panel is OLED.

The mesh panel assembly 150 in this exemplary embodiment includes planar layers 150A and 150B of transparent optically isotropic material, such as a glass, which sandwich a non-magnetic, electrically conductive mesh 150C. The opening size of the mesh is preferably sufficiently small so as to block RF signals from passing through, yet large enough to allow the optical image rays pass through. An exemplary mesh opening size is on the order of 50 mesh openings per square inch. The mesh may be fabricated from copper, tungsten or alloy thereof, for example. The mesh panel assembly 150 is constructed to be optically isotropic, i.e. with a refractive index not dependent on the polarization and propagation direction of light. If the mesh panel assembly 150 were to be anisotropic, and exhibit birefringence, this could affect the polarized light emitted from the panel 130 and destroy the 3D effect. The panel 150 could also be a single layer of optically isotropic material, on which the mesh is applied or etched. However, to protect the mesh from damage, sandwiching the mesh between two layers can be advantageous. High quality isotropic glass, and plastics such as isotropic acrylic and CR39, may be employed to form the window assembly 150.

In this exemplary embodiment, the display panel 130 is spaced from the mesh panel assembly 150 by an elastomeric spacer member 122. An EMI (electromagnetic interference) gasket 124A is positioned between adjacent surfaces of the edge of the mesh panel 150 and the inner surface of flange portion 120A1 of the internal mounting frame structure 120. Another EMI gasket 124B is positioned between adjacent portions of the back edge 112B of the cover structure 112 and the back flange portion 120C1 of the internal mounting frame structure 120. The EMI gaskets can be fabricated of a springy non-magnetic, electrically conductive material, such as a copper/bronze alloy.

The edges of the electrically conductive mesh layer 150C are brought into contact with the adjacent surface of the internal mounting frame structure 120, e.g. at 120D, so that the mesh is electrically connected to the internal mounting frame structure 120. A grounding connection 180 at the rear cover is connected to system ground within the magnet room so that the Faraday cage 110 is grounded.

A support structure 160 is positioned between a back panel portion 120B of the internal mounting frame structure 120 and the lower portion of the LED backlight 140. The support structure 160 is fabricated of a non-magnetic material such as aluminum. The top edge of the LED backlight is secured by a bracket portion 120A2 of the frame structure 120. A circuit board structure 170 is positioned with an upwardly extending board portion 170A positioned between the display panel 130 and the backlight panel 140. The board portion can include circuit traces for making electrical contact with the circuit of the display panel, for example. The particular technique for fabricating the display panel 130 and driving it to provide the 3D display images may be conventional.

An interface module 190 is positioned within the Faraday cage, adjacent the rear cover 116, and provides a power supply for the 3D flat panel display 100, and a connection (e.g. fiber optic, broadband Wi-Fi) for the video source signals to be supplied to the 3D flat panel display 100.

The 3D flat panel display 100 in this exemplary embodiment employs FPR technology to provide a 3D effect when used with an appropriate set of goggles or glasses, with circular polarization filters of opposite sense through which the image generated by the 3D display is viewed. Alternatively, the display could use left and right linear polarizations to produce the 3D effects, with corresponding left and right linear polarization on the polarized films applied to the goggles worn by the patient. Other display technologies could produce the 3D effect in conjunction with electronics to create the 3D effect on the display itself, without the need for the patient to wear polarized glasses. For example, parallax barrier, glasses-free displays are known, which work by placing an opaque screen door-like barrier over the screen. Each eye views the barrier from a slightly different angle, and therefore sees different sets of pixels behind it. Some manufactures use an LCD barrier that can be turned off to enable 2D viewing. In the case of the parallax barrier, glasses-free display, the patient might directly view the 3D image reflected from the mirror. In all cases, the optical path between the image panel generating the 3D images and the patient's eyes should not pass through birefringent materials, which may adversely affect the 3D content of the images.

Figure 4:
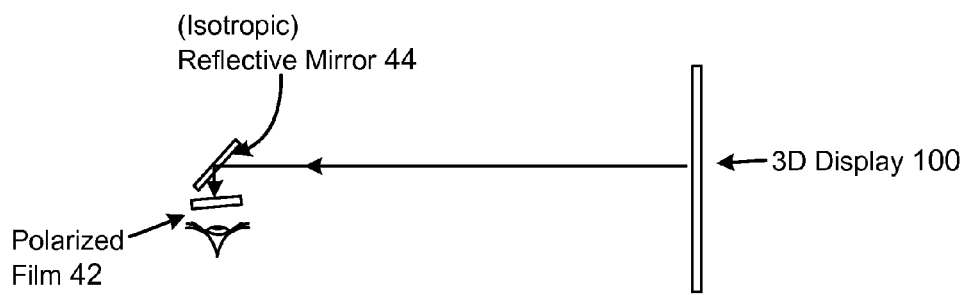
FIG. 4 is a diagrammatic depiction of a patient viewing a 3D display while lying in an MRI bore.

FIG. 4 diagrammatically illustrates how, in one exemplary embodiment, a patient in an MRI tunnel could view the 3D images generated by the 3D flat panel display 100. The patient wears the circular polarized passive glasses or goggles, with lenses having circular polarization filters of opposite polarization sense for the left and right eye, typically applied by a filter film, and through the use of a reflective mirror, can view the MRI-compatible display, e.g. a shielded LCD TV, located on either end of the MRI bore (tunnel). The glasses are configured to be MRI-compatible, without magnetic materials. Alternatively the circularly polarized filters can be built into the passive glasses or applied to the mirror which the patient looks into to see the display image. The patient can see the display while lying down on the MRI bore, using the combination of the polarized films in conjunction with the reflective mirror.

The reflective mirror 44 in the MRI bore is optically isotropic, i. e. with a refractive index not dependent on the polarization and propagation direction of light. Typically, the reflective surface is placed on a back side of the mirror substrate, to reduce chances of scratching or damaging the reflective surface (as compared to forming the reflective surface on the front face of the mirror substrate). A suitable exemplary plastic for the mirror substrate is acrylic or CR39. For the case in which the reflective surface is placed on the back surface of the mirror substrate, the light path is through the substrate, which in this case should be formed of an optically isotropic plastic material, to avoid affecting the 3D image content of the viewed image. If the reflective surface is placed on the mirror front face, then the light path does not pass through the mirror substrate, and the substrate material should have little effect on the image quality.

Although the foregoing has been a description and illustration of specific embodiments of the subject matter, various modifications and changes thereto can be made by persons skilled in the art without departing from the scope and spirit of the invention.

What is claimed is:

1. A display system compatible with a magnetic resonance imaging (MRI) apparatus disposed in a magnet room for producing video images to a patient in an MRI magnet tunnel, the images having a three-dimensional (3D) effect, the system comprising:
an MRI-compatible 3D display responsive to said video signals and disposed within said magnet room, said display including a display panel configured to generate optical images having 3D content, and RF and electromagnetic interference filtering to prevent noise from said display means from affecting the quality of the images produced by said MRI apparatus, the 3D display further including a Faraday cage structure comprising an optically transparent window panel, the display panel disposed within the Faraday cage structure, the window panel having an electrically conductive mesh having a mesh opening size sufficiently small to block RF signals generated by the display system from passing through the mesh and into the magnet room, and large enough to allow optical image rays from the display panel from passing through without, the window the optically transparent window panel comprising a transparent optically isotropic material allowing optical image rays pass through without significantly affecting the 3D content of the images.

2. The system of claim 1, wherein the optically transparent window comprises at least one layer of said transparent optically isotropic material, and said conductive mesh is adjacent a surface of said at least one layer.

3. The system of claim 2, wherein said at least one layer of said transparent optically isotropic material comprises a first layer and a second layer, and said conductive mesh is sandwiched between said first layer and said second layer.

4. The system of claim 3, wherein a peripheral edge of the conductive mesh is exposed at a peripheral edge of the window, and wherein a conductive adhesive is applied to the peripheral edge of the mesh and the peripheral edge of the window, such that with the window assembled in a conductive display housing, the edge of the window stays in tight electrical contact with the housing.

5. The system of claim 1, wherein the transparent optically isotropic material comprises a glass or a plastic material.

6. The system of claim 1, further comprising:
a mirror positioned in the MRI magnet tunnel so that the patient in the tunnel can view the 3D display, the mirror formed of a substrate of a non-magnetic optically isotropic material and a reflecting surface.

7. The system of claim 6, further comprising:
circular polarization filters of opposite sense for each patient eye and positioned so the patient views images generated by the 3D display and reflected from the mirror through the circular polarization filters to produce a 3D effect.

8. The system of claim 1, wherein the 3D display includes FPR (Film Patterned Retarder) technology to provide separate left and right eye images having 3D image content, and further comprising:
polarization filters of opposite sense for each patient eye and positioned so the patient views images generated by the 3D display and reflected from the mirror through the polarization filters to produce a 3D effect.

9. The system of claim 8, wherein the filters are formed on non-magnetic eyeglasses worn by the patient in the MRI magnet tunnel.

10. The system of claim 9, wherein the mirror formed of a substrate of a non-magnetic optically isotropic material and a reflecting surface.

11. The system of claim 8, wherein the polarization filters are formed on a mirror positioned in the MRI magnet tunnel so that the patient in the tunnel can view the 3D display.

12. A display system compatible with a magnetic resonance imaging (MRI) apparatus disposed in a magnet room for producing video images to a patient in an MRI magnet tunnel, the images having a three-dimensional (3D) effect, the system comprising:
   a 3D display responsive to said video signals and disposed within said magnet room, said display including a display panel configured to generate optical images having 3D image content with separate left and right eye images, the 3D display further including a Faraday cage structure in which the display panel is disposed, the cage structure comprising:
   an optically transparent window panel having an electrically conductive mesh with a mesh opening size sufficiently small to block RF signals generated by the display system from passing through the mesh and into the magnet room, and large enough to allow optical image rays from the display panel from passing through the window, the optically transparent window panel comprising a transparent optically isotropic material allowing optical image rays pass through without significantly affecting the 3D content of the images;
   a front cover structure which circumscribes a window panel area,
   a rear cover attached to a back of the front cover structure,
   an internal mounting frame structure positioned between the front cover structure and the rear cover to support the display panel and the window panel,
   the front cover structure, the rear cover and the internal mounting frame structure each fabricated of non-magnetic electrically conductive material.

13. The system of claim 12, wherein the window panel comprises at least one layer of said transparent optically isotropic material, and said conductive mesh is adjacent a surface of said layer.

14. The system of claim 13, wherein said at least one layer of said transparent optically isotropic material comprises a first layer and a second layer, and said conductive mesh is sandwiched between said first layer and said second layer.

* * * * *